(12) United States Patent  (10) Patent No.: US 8,917,105 B2
Gardell  (45) Date of Patent: Dec. 23, 2014

(54) SOLDER BUMP TESTING APPARATUS AND METHODS OF USE

(75) Inventor: David L. Gardell, Fairfax, VT (US)

(73) Assignee: International Business Machines Corporation, Armonk, NY (US)

(*) Notice: Subject to any disclaimer, the term of this patent is extended or adjusted under 35 U.S.C. 154(b) by 274 days.

(21) Appl. No.: 13/481,160

(22) Filed: May 25, 2012

(65) Prior Publication Data

US 2013/0314117 A1   Nov. 28, 2013

(51) Int. Cl.
G01R 1/067 (2006.01)

(52) U.S. Cl.
USPC ...... 324/755.01; 324/437; 324/445; 324/446; 324/754.01

(58) Field of Classification Search
CPC ........................................................ G01R 1/067
USPC ............... 324/437, 445, 446, 754.01–754.11, 324/754.21–755.07, 757.01–757.05
See application file for complete search history.

(56) References Cited

U.S. PATENT DOCUMENTS

| | | |
|---|---|---|
| 5,269,190 A | 12/1993 | Kramer et al. |
| 6,038,931 A | 3/2000 | Long et al. |
| 6,134,954 A | 10/2000 | Suresh et al. |
| 6,247,355 B1 | 6/2001 | Suresh et al. |
| 6,778,916 B2 | 8/2004 | Lee |
| 7,051,600 B1 | 5/2006 | Cavallaro et al. |
| 8,513,965 B2 * | 8/2013 | Breinlinger .............. 324/754.01 |
| 2004/0181403 A1 | 9/2004 | Hsu |
| 2006/0114008 A1 * | 6/2006 | Fujii ............................. 324/754 |
| 2007/0181304 A1 | 8/2007 | Rankin et al. |
| 2008/0088332 A1 * | 4/2008 | Beaman et al. ............... 324/762 |
| 2009/0266447 A1 | 10/2009 | Busby et al. |
| 2010/0078206 A1 * | 4/2010 | Fan et al. ...................... 174/261 |

FOREIGN PATENT DOCUMENTS

| | | | |
|---|---|---|---|
| JP | 2000088722 A | 3/2000 |
| JP | 2005337812 A | 12/2005 |
| JP | 2007248439 A | 9/2007 |
| JP | 2008252053 A | 10/2008 |

* cited by examiner

Primary Examiner — Arleen M Vazquez
Assistant Examiner — Alesa Allgood
(74) Attorney, Agent, or Firm — Michael LeStrange; Roberts Mlotkowski Safran & Cole, P.C.

(57) ABSTRACT

A testing apparatus for measuring the material properties of solder balls includes a frame and a chuck base moveable in X, Y, Z dimensions, relative to the frame. A probe tip is fixed to the frame. A measuring device is mounted to the frame and maintains a spacing with relationship to the probe tip and which has an initial, known height above the chuck base.

14 Claims, 7 Drawing Sheets

SOLDER BUMP TESTING APPARATUS AND METHODS OF USE

FIELD OF THE INVENTION

The invention relates to a semiconductor testing apparatus and, more particularly, to solder bump compressive testing apparatus and methods of use.

BACKGROUND

It is important to characterize hardness of solder bumps in order to evaluate the feasibility of testing chips with non-compliant wafer test probes because they rely on compression of the solder bump to overcome non-planarity of the solder bumps. Lead free solders can be significantly harder than the lead tin solder bumps. Thus, lead free testing may require forces that are beyond the capability of existing test equipment and the structural strength of the chip dielectric layers. Also, known tools for characterizing solder bump hardness do not deform the solder ball in the same manner as the non-compliant wafer probes. Accordingly, there is no practical way to characterize the hardness of individual lead free solder bumps.

Accordingly, there exists a need in the art to overcome the deficiencies and limitations described hereinabove.

BRIEF SUMMARY

In an aspect of the invention, a testing apparatus comprises a probe tip and a chuck base moveable in X, Y, Z dimensions, relative to the probe tip. A measuring device is mounted on the chuck base. A mechanism maintains a spacing with relationship between the probe tip and measuring device.

In an aspect of the invention, a testing apparatus comprises a computing infrastructure which receives a force measurement applied on a solder bump and a deflection of the solder bump when the force is applied. The computing infrastructure generates a plot of the force vs. deflection in order to determine a hardness of the solder bump.

In an aspect of the invention, a method comprises: compressing a ball of ductile material with a probe tip; recording a force applied to the ductile material and distance the probe is displaced; and determining hardness, compressive yield strength and height of the ductile material based on the force and the displacement.

BRIEF DESCRIPTION OF THE SEVERAL VIEWS OF THE DRAWINGS

The present invention is described in the detailed description which follows, in reference to the noted plurality of drawings by way of non-limiting examples of exemplary embodiments of the present invention.

DETAILED DESCRIPTION

The invention relates to a semiconductor testing apparatus and, more particularly, to solder bump testing apparatus and methods of use. More specifically, the present invention is directed to a solder bump compressive testing apparatus and method of use. The solder bump testing compressive apparatus can measure the hardness (stiffness), the change in height over time (creep) and height of individual solder bumps. In turn, the present invention can use this information to characterize and optimize the lead free alloy and heat treatments for minimum hardness, as an illustrative example. Other uses of this information are to design non-compliant wafer probe systems for wafer test.

In embodiments, the solder bump testing apparatus includes a load cell that can compress individual solder bumps mounted on a wafer or chip. In embodiments, the tip of the load cell can be precisely aligned to a single solder bump, e.g., C4, using a dual axis optical system. More specifically, to precisely measure the height and hardness of individual solder bumps, a clamping mechanism holds the semiconductor device under test (e.g., wafer) to a chuck during the testing. In embodiments, the clamping mechanism can be, for example, a vacuum chuck. The chuck, in turn, is mounted to a stage which is moveable in the X, Y and Z directions. This allows the solder bump to be aligned and then raised into contact with the load cell while recording force imposed on the solder bump. The force imposed on the solder bump will result in a deflection (compression) of the solder bump. In embodiments, the load cell is attached to a support frame which also provides X, Y alignment features for the Z height measurement means which slides on the chuck when moving to a next solder bump for testing.

In embodiments, the load cell of the testing apparatus applies a vertical force to each individual solder bump deposited on the semiconductor device under test. A displacement arm coupled to a precision measuring device records a distance the load cell tip is displaced relative to the chuck when the load cell force is applied to the semiconductor device under test, e.g., each solder bump. This displacement is measured and plotted to provide solder bump stiffness, as disclosed in more detail below. For example, the data can be plotted to provide a slope, which is representative of solder bump stiffness (hardness).

Advantageously, the solder bump testing apparatus and methods of use avoid many of the shortcomings of known systems and measurement methods. For example, conventional indentation hardness testers are not suitable for small samples. Micro-indentation testers require extensive sample preparation (potting and lapping) and results will not be comparable to deflection seen with rigid wafer probe systems. Conventional compression testing machines measure cross head or fixture movement thus the measured compression includes deflection of the load cell and support fixture, which is a significant source of error when total deflection is measured in microns. Alignment of the probe tip to the solder ball in conventional test systems is also tedious, especially when it is desirable to measure a large sample of solder balls. Moreover, it is now possible to test individual solder bumps, instead of using a rigid ceramic pedestal substrate which proves difficult to use due to co-planarity from probe to probe (e.g., from different height solder bumps). Also, by eliminating the use of the rigid ceramic pedestal substrate, parallelism and co-planarity errors no longer have to be absorbed by compression of the solder bumps. Instead, the testing apparatus can accurately and precisely measure any and all of the solder bumps, individually, regardless of a variance in height of each individual solder bump. Also, it is now possible to measure multiple solder bumps on one chip much faster, compared to conventional systems.

Figure 1:
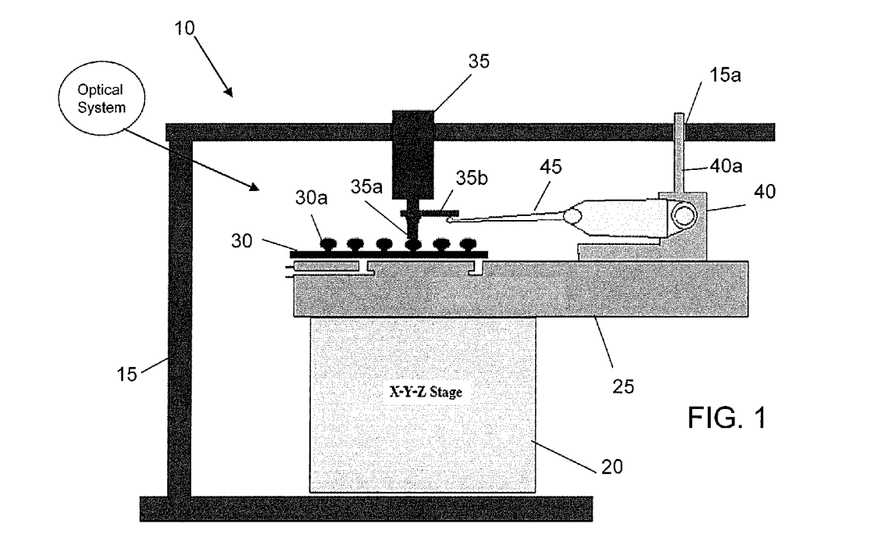
FIG. 1 shows a testing apparatus in accordance with aspects of the present invention.

FIG. 1 shows a testing apparatus in accordance with aspects of the present invention. More specifically, the testing apparatus 10 includes a frame 15, with a stage 20 mounted to the frame 15. A chuck base 25 is mounted to the stage 20. In embodiments, the stage 20 can move the chuck base 25 in the X, Y, Z dimensions, relative to the frame 15. In embodiments, the chuck base 25 can be a vacuum base, which is structured to hold a wafer 30 or portion thereof. In embodiments, other mechanical mechanisms can be used to hold the wafer 30 to the chuck base 25, for example, straps, adhesive, etc. In embodiments, the chuck base 25 is a rigid, flat metal or metal alloy. The chuck base 25 can also be temperature controlled in order to provide solder bump measurements (e.g., deflection of solder bumps) at different temperatures.

Still referring to FIG. 1, a load cell 35 is affixed to the frame 15. In embodiments, the load cell 35 can be any conventional load cell, e.g., spring loaded cell, having a tip 35a contacting a solder bump 30a mounted on the wafer 30. The tip 35 can comprise many different geometries such as, for example, pointed, rounded and flat; although a flat tip has been found to provide the most repeatable results. In embodiments, the load cell 35 will be used to measure the force applied to deflect (compress) the solder bumps 30a by a certain amount, upon the application of a force applied by, e.g., raising the chuck base 25 mounted on the stage 20 in the Z direction. In embodiments, the solder bump 30a is a ductile material comprising a controlled collapse chip connection (C4) solder bump used in semiconductor flip-chip packaging. The load cell tip 35a also includes a rigid, outwardly extending arm 35b. In embodiments, the rigid, outwardly extending arm 35b is solid, with no discernable flexure upon the application of a force.

A test stand 40 is placed on the chuck base 25. In embodiments, the test stand 40 can be moved relative to the chuck base 25 in the X-Y directions. In further embodiments, the test stand 40 includes pins 40a, e.g., two pins, which extend through corresponding holes 15a within the frame 15. The test stand 40 can also be mounted to the frame 15 using other mechanisms, known to those of skill in the art. In this way, the relative position of the test stand 40 and the load cell 35 will always remain the same, thereby ensuring that a measuring device (with outwardly extending displacement arm) 45 mounted on the test stand 40 will remain in contact with the rigid, outwardly extending arm 35b, e.g., when the chuck base 25 is moved with stage 20 so that the next solder bump can be tested.

In embodiments, the measuring device 45 can be, for example, a mechanical device, a laser, an optical device, a capacitive device, an inductive device, etc., any of which provides a direct height measurement of the solder bump 30a. In embodiments, the measuring device 45 is provided at a known, predetermined height with respect to the chuck base 25, and is positioned under the rigid, outwardly extending arm 35b, preferably in contact therewith, prior to a force being applied by the load cell 35. It will be recognized that measuring device 45 will measure the deflection of the solder ball 30a relative to chuck base 25 and will be unaffected by deflections within the load cell 35 and frame 15. An optical system 100 can be provided to align the solder bump 30a with the tip 35a. In one implementation, orthogonal optical systems are used to align the tip with the rows and columns of C4s on the chip or wafer.

In operation, the solder bump 30a is aligned with the tip 35a of the load cell 35 by moving the stage 20 in X, Y dimensions (using the optical system 100). In embodiments, the stage 20 can be moved by any motive mechanism such as, for example, micrometer, a linear motor, rack and pinion gear system and the like. In embodiments, an encoder can be used to precisely move the stage 20 by a required distance. Prior to exerting a force on the solder bump 30a, the load cell 35 may read a very small value from the force of the indicator arm (measuring device) 45. Once the solder bump 30a and the tip 35a are aligned, the stage 20 can be raised, e.g., moved in the Z dimension, so that the tip 35a comes in contact with the solder bump 30a. At this initial contact, the measuring device 45 can provide an initial reading of the height of the solder bump 30a. This can be achieved by activating the measuring device 45 upon an initial force reading of the load cell 35. More specifically, as the initial height from the base is known, the height of the solder bump can easily be calculated by a simple subtractive method with relationship to the load cell, which remains in contact with the measuring device.

Continuing with the operation, as the stage 20 continues to be raised, a force will be exerted on the solder bump 30a, which is measured by the load cell 35. As the force continues to be applied, the solder bump 30a becomes compressed, e.g., deflects downward with respect to the wafer 30. This compression, in turn, results in a reduced distance between the measuring device 45 and the surface of the chuck base 25 (measured by a reduced distance of the load cell with relation to the chuck base, as measured by the measuring device). The measuring device 45, of course, can measure this reduced distance, which can then be plotted against the applied force to provide a hardness of the solder bump 30a. More specifically, the measuring device 45 can measure the displacement of the solder bump 30a, relative to the initial distance from the chuck base 25. In an alternate embodiment, the measuring device 45 measures tip movement relative to the initial position when the tip first touched the solder ball In one illustrative exemplary embodiment, the following conditions were provided for the wafer under test:

The load cell provided a force of up to 60 gms with +/−0.01 gms resolution;

The displacement of the solder bump can be up to 43 um with +/−0.02 um resolution;

The test was provided at room temperature, without the need to have any initial height data or electrical contact data;

The test provided automatic data collection using a computing infrastructure as described with reference to FIG. 5; and The stage was raised at 10 gms/sec at max rate; although other rates were found to not have any significant effects on the test results of this particular alloy and test temperature.

In yet another embodiment, the stage is raised to one height and force and deflection is recorded vs. time as a measure of creep properties. In this embodiment, the deflection continues to increase over time, which causes the load to decrease over time due to the stiffness of the load cell and frame. In comparison, in conventional testing it is generally preferable to characterize creep at either constant force or constant deflection. A feedback to the Z stage can be provided to maintain creep at either constant force or constant deflection.

Figure 2:
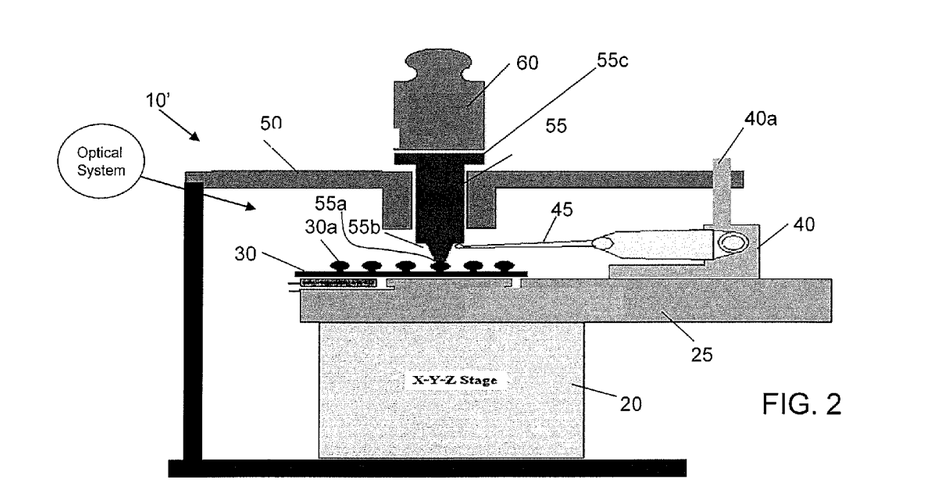
FIG. 2 shows an alternative testing apparatus in accordance with aspects of the present invention.

FIG. 2 shows an alternative dead weight testing apparatus in accordance with aspects of the present invention. The dead weigh implementation is preferable for creep testing. In this embodiment, the load cell of FIG. 1 is replaced with a bearing frame 50 and anvil 55. The testing apparatus 10' includes a test stand 40 fixed relative to a support and bearing frame 50. Similar to that shown in FIG. 1, the test stand 40 can be fixed to the support and bearing frame 50 by one or more pins 40a. In addition, in the embodiments shown in FIG. 2, an anvil 55 will maintain the same X-Y relative position with respect to the test stand 40. In embodiments, the anvil 55 can have a flat tip 55a and a ledge 55b for accommodating (contacting) the measuring device 45. As in the previous embodiment, the ledge 55b will be rigid, with no discernable flexure upon the application of a force, and the measuring device 45 will be provided at a known distance from the surface of the chuck base 25. A dead weight 60 can be provided on the anvil 55, in order to provide a known force. An optical system 100 can be provided to align the solder bump 30a with the tip 55a. Whereas anvil 55 is free to move upward (Z) in bearing 50, a stop 55c will limit downward movement of anvil 55 in bearing 50.

In operation using the test structure 10' of FIG. 2, the solder bump 30a is aligned with the anvil tip 55a by moving the stage 20 in X, Y dimensions. Once the solder bump 30a and the anvil tip 55a are aligned, the stage 20 can be raised, e.g., moved in the Z dimension, so that the anvil tip 55a comes in contact with the solder bump 30a. As the stage 20 continues to be raised, a force will be exerted on the solder bump 30a, which is applied by the anvil 55 and the weight 60. Further upward movement will cause the anvil stop 55c to rise off the bearing 50 thus signaling that all the weight of the anvil 55 and dead weight 60 is supported by the solder ball 30a. As the force continues to be applied, the solder bump 30a becomes compressed. The indicator 45 will record this deflection as a function of time (creep). In embodiments, the procedure can be repeated with a heavier dead weight and the hardness can be calculated from the difference in force divided by the difference in deflection. It has been determined that the most accurate results are obtained when the stage is lowered before adding or removing weights to the anvil.

In one illustrative exemplary embodiment, the following conditions were provided for the wafer under test using the testing apparatus 10' of FIG. 2:

The weight provided a force of 400 gms; and

The test provided automatic data collection using a computing infrastructure as described with reference to FIG. 5.

Thus, as should be understood by those of skill in the art, a method of measuring hardness and creep of any ductile material (using the testing apparatus of either FIG. 1 or FIG. 2) comprises compressing a solder bump or ball comprising the ductile material with a flat anvil or load cell tip (generally "probe tip"). The force applied to the ductile material and distance the anvil or load cell is displaced is measured to determine hardness of the material. The method further includes plotting the anvil or load cell force and displacement, and determining the hardness of the ductile material as the slope of the applied force versus displacement. Creep is determined from the change in height over time with a constant load. It will be recognized by those of skill in the art that other arrangements of the parts are possible, for example the chuck could be stationary with the load cell mounted to a X-Y Z stage or X and Y could be on one stage and Z on another.

Figure 3:
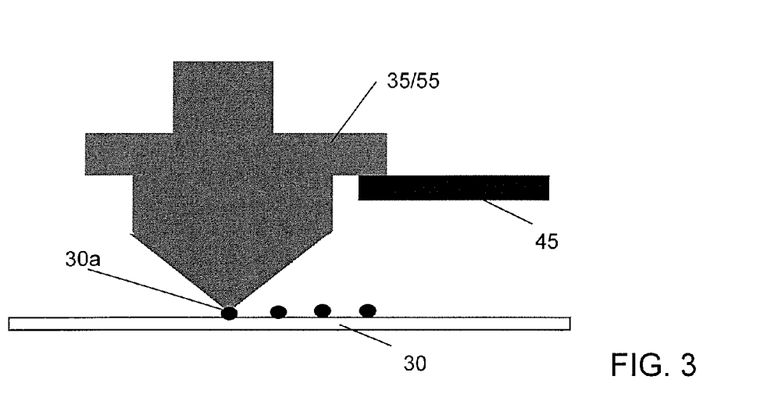
FIG. 3 shows an enlarged sectional view of a tip of the testing apparatus of FIG. 1 or FIG. 2, in accordance with aspects of the present invention.

FIG. 3 shows an enlarged sectional view of a tip of the testing apparatus of FIG. 1 or FIG. 2, in accordance with aspects of the present invention. More specifically, FIG. 3 shows an alignment with the load cell tip 35a or the anvil tip 55a with a solder bump 30a of the wafer 30. As representatively shown, the testing apparatus of FIGS. 1 and 2 can be precisely aligned with a solder bump 30a. In this way, the testing apparatus of FIGS. 1 and 2 can accurately and precisely measure the initial height, deflection and hardness of individual solder bumps, without interfering data being obtained from other solder bumps.

Figure 4A:
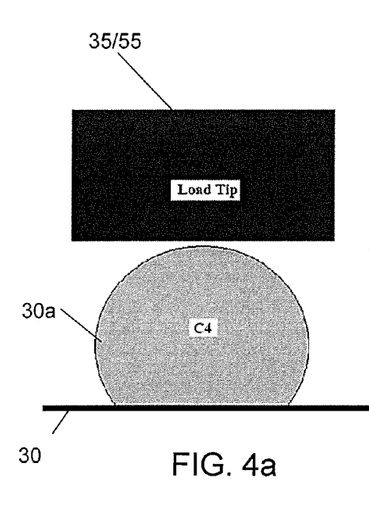
FIGS. 4a and 4b show a representative geometric model of the tip of the testing apparatus of FIG. 1 or FIG. 2 pressing against a solder bump, in accordance with aspects of the present invention.
Figure 4B:
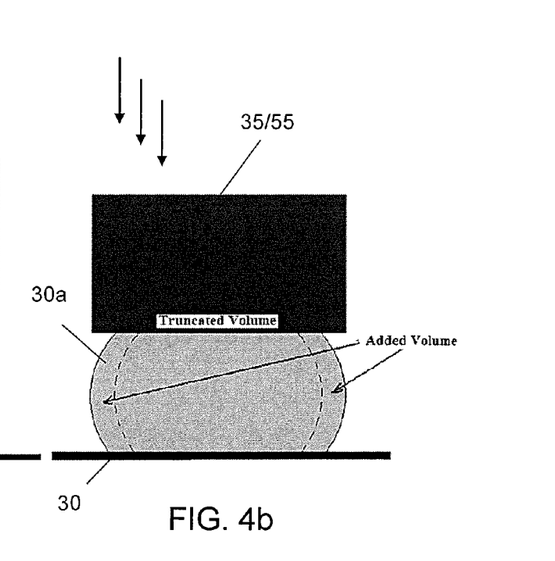

FIGS. 4a and 4b show a representative geometric model of the tip of the testing apparatus of FIG. 1 or FIG. 2, pressing against a solder bump in accordance with aspects of the present invention. More specifically, FIG. 4a shows the tip of the testing apparatus prior to making contact with the solder bump 30a. In FIG. 4b, the tip of the testing apparatus is making contact with the solder bump 30a. This results in a flattened contact area on the top of the ball and also has the effect of increasing the ball diameter. The resulting diameter of the contact area can be calculated from the initial ball diameter, height and the change in height assuming a conservation of solder volume. The contact area can be multiplied by the compressive yield strength to predict the force vs. deflection of the solder ball.

Figure 4C:
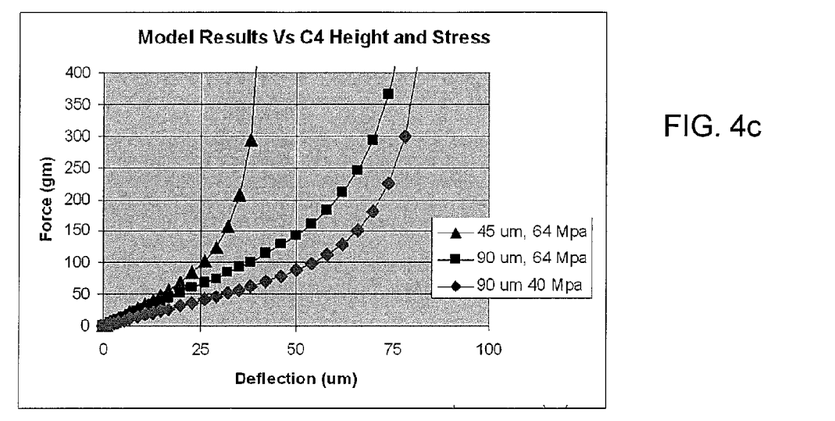
FIG. 4c is an example of force vs. deflection calculated from a geometric model for different size and material solder bumps as provided in accordance with aspects of the present invention.
Figure 4D:
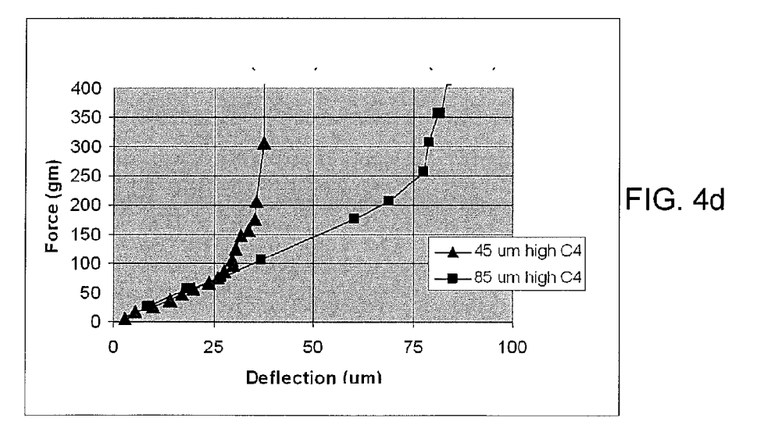
FIG. 4d is measured data demonstrating slope being a function of material type and independent of ball size as predicted by the geometric model and provided in accordance with aspects of the present invention.

FIG. 4c is an example of calculated force vs. deflection for different size and material solder balls (bumps). This lead to the discovery that slope is mostly a function of material type and to a much less extent the size of the ball. FIG. 4d is measured data demonstrating this discovery, with bumps of the same material but different size were found to have the same initial slope. It will now be recognized by one skilled in the art that the present invention can thus be used to calculate the compressive yield strength from the measured force and deflection, and that the results will be relatively independent of the size of the ball.

As will be appreciated by one skilled in the art, and as described with reference to FIG. 5, aspects of the present invention may be embodied with a system or computer program product. Accordingly, aspects of the present invention may take the form of an entirely hardware embodiment, an entirely software embodiment (including firmware, resident software, micro-code, etc.) or an embodiment combining software and hardware aspects. Furthermore, aspects of the present invention may take the form of a computer program product embodied in one or more computer readable medium(s) having computer readable program code embodied thereon. Any combination of one or more computer readable medium(s) may be utilized. The computer readable medium may be a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Figure 5:
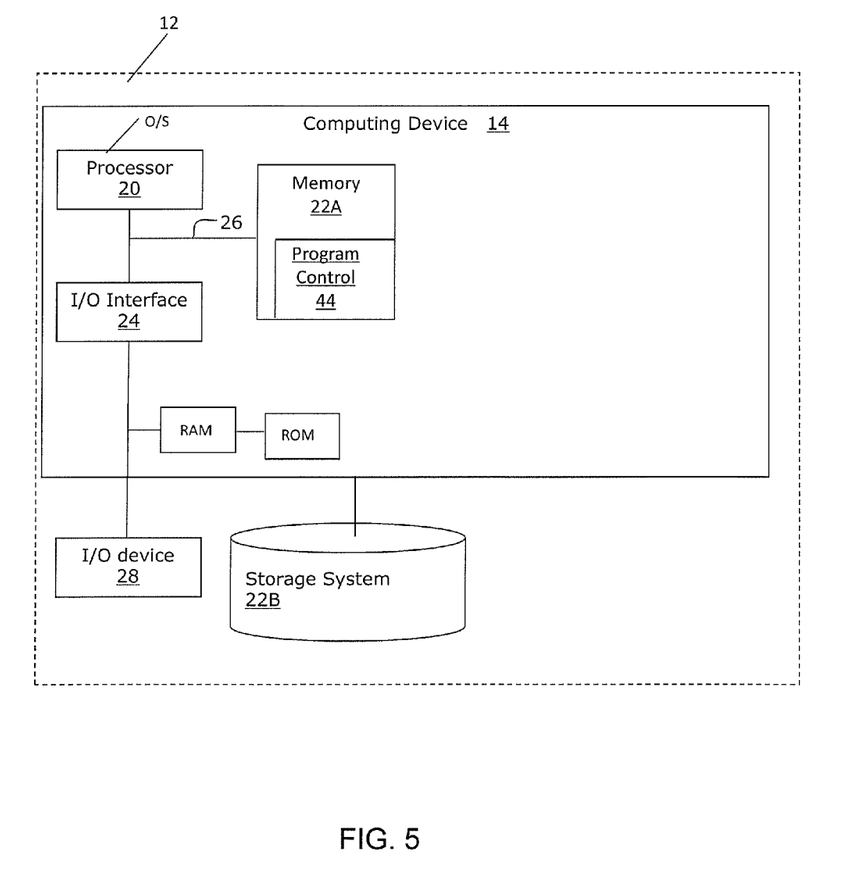
FIG. 5 shows a computing infrastructure which can be implemented with the testing apparatus in accordance with aspects of the invention.

FIG. 5 shows a computing infrastructure which can be used with the testing apparatus of FIG. 1 or FIG. 2. The computing infrastructure 12 can be used to automatically obtain the measurement and/or force data, and translate such data into the plots shown in FIGS. 6-10. That is, the computing infrastructure 12 can be used to calculate the hardness of the solder bumps, amongst other material properties as described below. To this extent, computing infrastructure 12 is a server or other computing system that can perform the processes described herein. The computing infrastructure 12 includes a computing device 14, which can be resident on a network infrastructure or computing device of a third party service provider (any of which is generally represented in FIG. 1).

The computing device 14 includes a processor 20, memory 22A, an I/O interface 24, and a bus 26. The memory 22A can include local memory employed during actual execution of program code, bulk storage, and cache memories which provide temporary storage of at least some program code in order to reduce the number of times code must be retrieved from bulk storage during execution. In addition, the computing device includes random access memory (RAM), a read-only memory (ROM), and an operating system (O/S). The computing device 14 is in communication with the external I/O device/resource 28 and the storage system 22B. For example, the I/O device 28 can comprise any device that enables an individual to interact with the computing device 14 (e.g., user interface) or any device that enables the computing device 14 to communicate with one or more other computing devices using any type of communications link. The external I/O device/resource 28 may be for example, a handheld device, PDA, handset, keyboard (data acquisition system connected to the load cell and indicator), etc.

In general, the processor 20 executes computer program code (e.g., program control 44), which can be stored in the memory 22A and/or storage system 22B. The computer program code can be computer program instructions stored in the memory 22A or storage system 22B or computer readable medium that can direct the computing device 14, other programmable data processing apparatus, or other devices to function in a particular manner. Moreover, in accordance with aspects of the invention, the program control 44 can be implemented as separate dedicated processors or a single or several processors to provide the functions of the present invention. While executing the computer program code, the processor 20 can read and/or write data to/from memory 22A, storage system 22B, and/or I/O interface 24. The program code executes the processes of the invention. The bus 26 provides a communications link between each of the components in the computing device 14.

Figure 6:
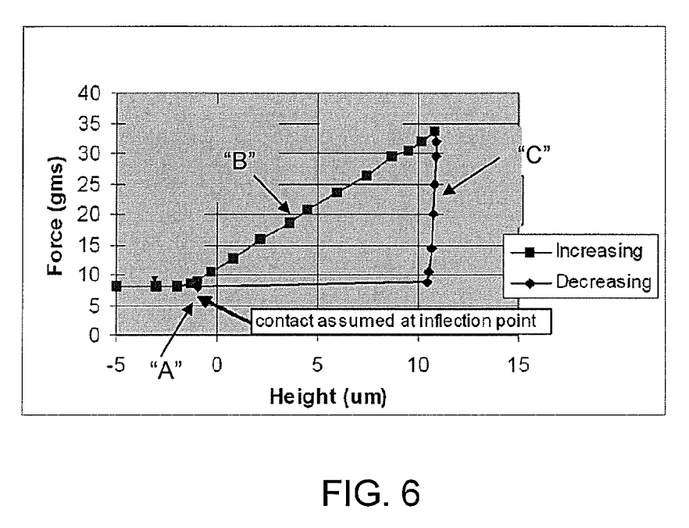
FIG. 6 shows a graph of measured raw sensor data in accordance with aspects of the present invention.

FIG. 6 shows data measured in accordance with aspects of the present invention. In FIG. 6, the y-axis is force (gms) and the x-axis is a deflection of the solder bump (in microns). The data points in FIG. 6 are for a single loading and unloading cycle for a solder bump, e.g., C4 bump. The base chuck 25 is raised using the stage 20, and data collection starts before the tip has contacted the C4 bump. The initial force of 7 gms is due to the force from the height indicator, the very small initial slope is the change in indicator force vs. deflection. In one implementation, the change in force from the indicator can be subtracted from the load measured during the C4 bump compression.

As shown in FIG. 6, at the inflection point "A", the load cell tip (or anvil) makes initial contact with the solder bump. As the force is increased, by raising the chuck, the deflection of the solder bump increases in a linear fashion; although the deflection can be non-linear in different alloys Illustratively as shown in this graph, the slope of line "B" is approximately 2 gms/micron. This slope is representative of the solder bump hardness under test. At a force of approximately 34 gms, the force is reduced by lowering the stage. This line is essentially vertical indicating negligible elastic recovery of the solder bump, as represented in line "C".

If another C4 is tested, the change in the height of the inflection points (or change in height at some specific force) is a measure of the difference in height of the two C4 bumps. This has advantages over other known C4 bump height measurement methods such as laser, optical or surface profilmeters which can have difficulty measuring C4 bump heights due to small irregularities in surface contour, roughness, oxide layers and reflectivity. If the tip is brought into contact with the wafer surface near the C4 then the tool can also accurately measure the absolute height of each C4 bump.

Figure 7:
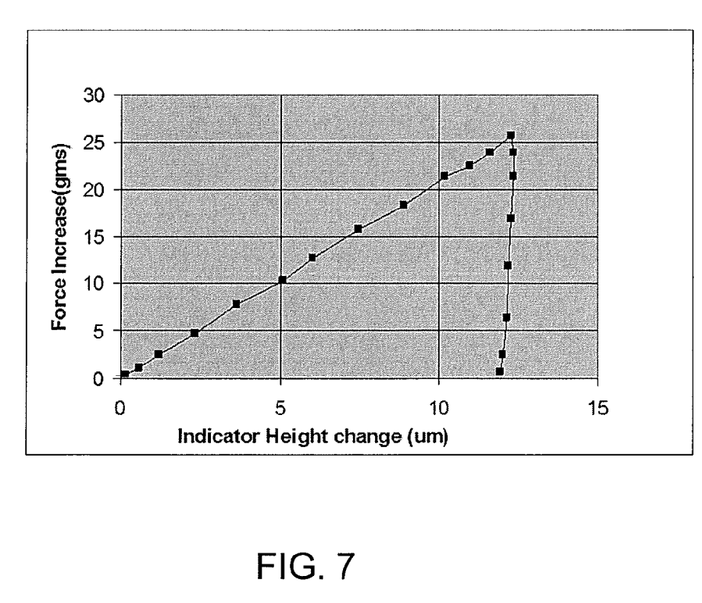
FIG. 7 shows data of FIG. 6 adjusted for initial contact in a plot of applied force vs. deflection, generated in accordance with aspects of the present invention.

FIG. 7 shows a graph of the same data from FIG. 6, where all data points have been shifted so the inflection contact point is at the origin. This is convenient to show data from multiple C4 bumps on one plot where differences in slope and shape of the curve are of most interest.

Figure 8:
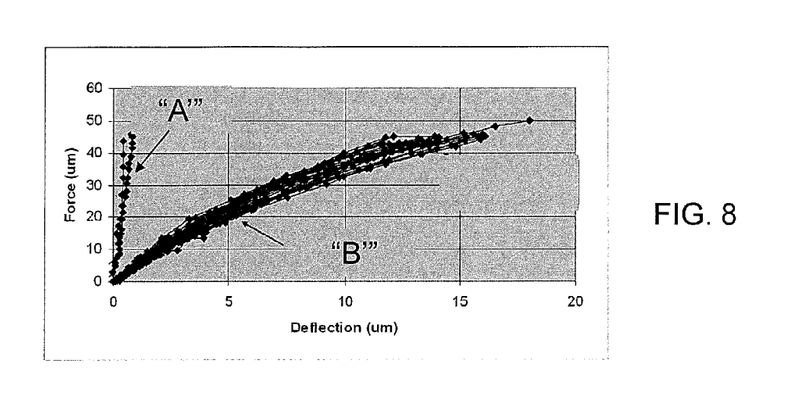
FIG. 8 shows a graph of multiple solder bumps tested in accordance with aspects of the present invention.

FIG. 8 shows a similar graph of 31 different solder bumps, shown at B, on one chip with a different lead free alloy and heat treatment (compared to FIG. 7). These bumps have a slight non linearity and harder composition. Also shown on FIG. 8 is the stiffness as measured directly on the chip surface adjacent to a solder ball, shown at A. This is the stiffness of the wafer, and probe tip and is similar in magnitude to the unloading portion C of FIG. 6. The wafer stiffness is so much higher than the solder ball it is often ignored. In one embodiment, the stiffness of the solder ball is corrected for the deflection of the wafer by subtracting the wafer deflection A from solder ball deflection B at each force.

Figure 9:
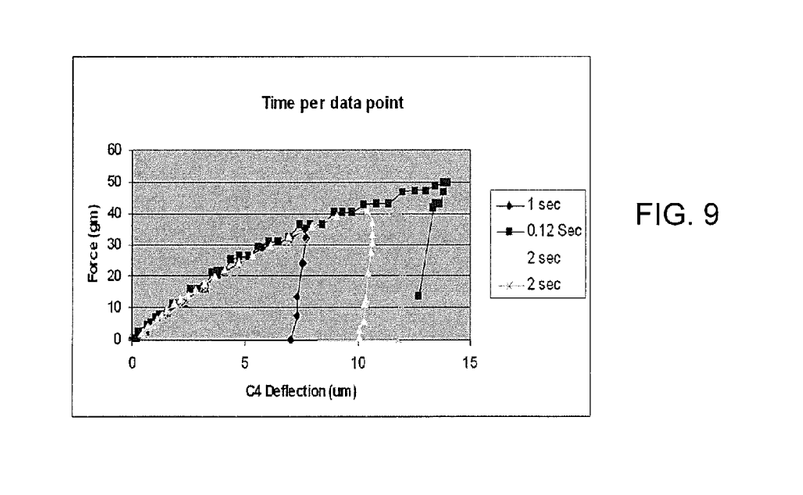
FIG. 9 shows a plot of solder bumps tested at various strain rates measured in accordance with aspects of the present invention.

FIG. 9 shows a plot measured in accordance with aspects of the present invention. In FIG. 9, four samples from the same chip are tested at different strain rates with the y-axis representing force (gms) and the x-axis representing deflection (microns). In this test, the total test time ranged from about four seconds to 80 seconds. As shown in the graph, the hardness of this alloy is not dependent on strain rate; that is, the slope of the lines for each of the solder bumps under test remained substantially the same regardless of time. Thus, it is shown that the testing apparatus can determine the effect of strain rate on hardness.

Figure 10:
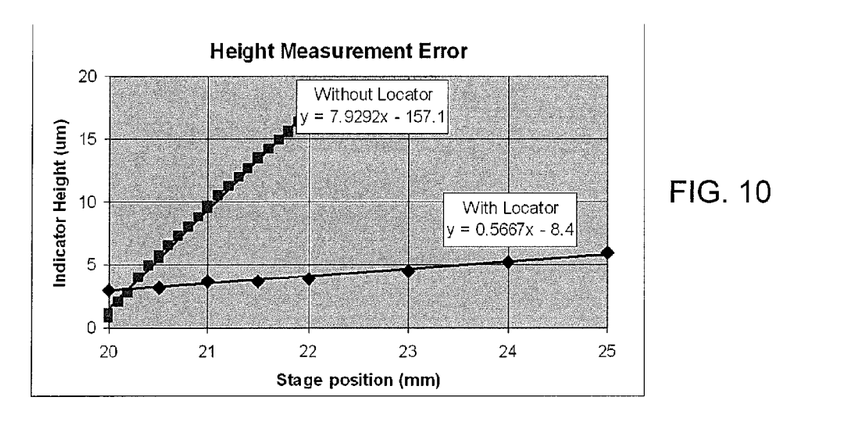
FIG. 10 shows a surface planarity graph generated in accordance with aspects of the present invention.

FIG. 10 shows height measurement error in accordance with aspects of the present invention. More specifically, in this graph, the measuring device (indicator height) is measured (in microns) against movement of the stage (in mm). Data is shown with and without the alignment locator features 15a and 40a of FIGS. 1 and 2. As shown, as the probe tip is moved above different solder bumps on the wafer, the measuring device measured a variance in tip height between adjacent solder bumps. With the locator pin 40*a*, there is a height error of only about 0.14 um between adjacent solder bumps on a 245 um spacing. As should now be understood, the alignment locator provides for very accurate measure of the relative height of adjacent C4s.

Figure 11:
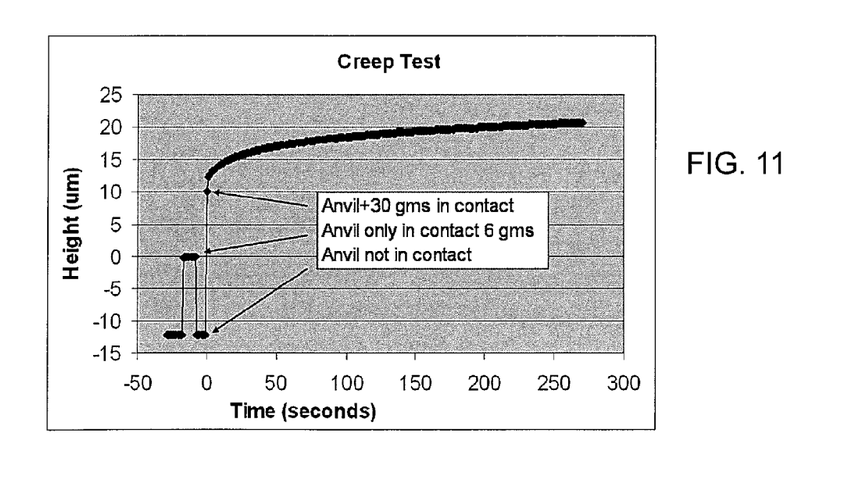
FIG. 11 shows a creep graph generated in accordance with aspects of the present invention.

FIG. 11 shows a typical dead weight test for creep. The height is first adjusted to zero when the anvil is resting on the C4. Initially the stage is lowered and a C4 is aligned with the anvil, the stage is raised to verify the anvil only reading (o um in this case), the stage is then lowered and a 30 gm weight is added to the anvil. When the stage is raised, deflection is recorded as a function of time. At any given point in time the stiffness can be calculated as the force increase of 30 gms divided by deflection. It should be understood by those of skill in the art that there are various ways the data can be analyzed and plotted for example log-normal or log-log plot. Stress can be calculated based on contact area and strain can be calculated from change in height and initial height.

The method as described above is used to characterize the C4s used in the fabrication of integrated circuit chips. C4s can be characterized for hardness, creep and height. This characterization enables the optimization of C4 design and construction to create C4s that can be tested (using a separate wafer test tool) for electrical performance before being diced and packaged. This characterization is especially important for wafer test systems that utilize non-compliant wafer probes and lead free C4s. The characterization is also important to ensure that the C4s are soft enough that they will not damage the device during test or packaging, a well known problem commonly referred to as white bumps. Generally this characterization is done during the development and qualification phases of a new product development and is not necessary during normal high volume manufacturing, except as a process monitor. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor. As should be now by recognized by those of skill in the art, the present invention could be used to characterize other ductile or elastic or elastic-plastic materials for other purposes.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed:

1. A testing apparatus, comprising:
   a probe tip;
   a chuck base moveable in X, Y, Z dimensions, relative to the probe tip;
   a measuring device mounted on the chuck base; and
   a mechanism to maintain a spacing with relationship between the probe tip and the measuring device, wherein:
   the measuring device comprises a displacement arm to record a distance the probe tip is displaced relative to the chuck base when a force is applied to a solder bump;
   a load cell comprising the probe tip, the load cell measures a force applied to the solder bump when the chuck base is moved towards the load cell; and
   the load cell includes a rigid, outwardly extending arm, which maintains contact with the displacement arm of the measuring device, such that movement of the load cell with relation to the solder bump can be measured.

2. The testing apparatus of claim 1, wherein the chuck base is a vacuum base, which holds a wafer or section of wafer with solder bumps thereon.

3. The testing apparatus of claim 1, wherein the movement of the displacement arm is caused by a deflection of the solder bump.

4. The testing apparatus of claim 1, further comprising an optical device to align the probe tip with the solder bump.

5. The testing apparatus of claim 1, further comprising a computing infrastructure to determine a hardness of the solder bump based on a measured force applied on the solder bump and displacement of the solder bump.

6. The testing apparatus of claim 1, wherein the measuring device remains stationary relative to the probe tip while the chuck base moves in the X, and Y, dimensions.

7. The testing apparatus of claim 1, wherein chuck base is a temperature controlled chuck base.

8. A testing apparatus, comprising:
   a probe tip;
   a chuck base moveable in X, Y, Z dimensions, relative to the probe tip;
   a measuring device mounted on the chuck base; and
   a mechanism to maintain a spacing with relationship between the probe tip and the measuring device; and
   an anvil which comprises the probe tip, wherein:
   the anvil is free to move in a vertical direction within limits defined by stops, and a dead weight provides a constant, known force on the anvil;
   the anvil maintains a same X-Y relative position with respect to a test stand;
   the anvil includes a ledge for contacting the measuring device;
   the ledge is rigid, with no discernable flexure upon the application of the constant, known force;
   the measuring device is provided at a known distance from a surface of the chuck base;
   an optical system aligns a solder bump with the probe tip; and
   the anvil is free to move upward in a bearing.

9. A testing apparatus comprising a computing infrastructure which receives a force measurement applied on a solder bump and a deflection of the solder bump when the force is applied, the computing infrastructure generating a plot of the force vs. deflection in order to determine a hardness of the solder bump, wherein the hardness of the solder bump is a slope of a plot.

10. The testing apparatus of claim 9, wherein the computing infrastructure provides a calibration measurement based on a deflection of a probe tip on the solder bump.

11. The testing apparatus of claim 10, wherein the computing infrastructure determines when a probe tip is provided on the solder bump or a wafer.

12. The testing apparatus of claim 11, wherein a testing to determine if hardness of the solder bump is independent of test time and creep properties are determined from force and deflection measured versus time.

13. A method comprising:
compressing a ball of ductile material with a probe tip;
recording a force applied to the ductile material and distance the probe is displaced; and
determining hardness, compressive yield strength and height of the ductile material based on the force and the displacement, wherein:
a displacement arm measures the distance the probe is displaced;
a load cell associated with the probe tip measures the force applied to the ductile material; and
an outwardly extending arm which maintains contact with the displacement arm measures movement of the load cell with relation to the ductile material.

14. The method of claim 13, wherein the deflection is measured as a function of time and optionally temperature to determine creep properties of the ductile material.

* * * * *